US012616964B2

(12) United States Patent
Zheng et al.

(10) Patent No.: US 12,616,964 B2
(45) Date of Patent: May 5, 2026

(54) SPIROCYCLIC COMPOUND CONTAINING CATALYST FOR USE IN CATALYZING REACTION OF EPOXIDE COMPOUND AND CARBON DIOXIDE

(71) Applicant: SHENZHEN CAPCHEM TECHNOLOGY CO., LTD., Shenzhen (CN)

(72) Inventors: Zhongtian Zheng, Shenzhen (CN); Tianqian He, Shenzhen (CN); Yuanyuan Kang, Shenzhen (CN); Qiyou Huang, Shenzhen (CN)

(73) Assignee: SHENZHEN CAPCHEM TECHNOLOGY CO., LTD., Shenzhen (CN)

( * ) Notice: Subject to any disclaimer, the term of this patent is extended or adjusted under 35 U.S.C. 154(b) by 467 days.

(21) Appl. No.: 18/044,219

(22) PCT Filed: Oct. 28, 2022

(86) PCT No.: PCT/CN2022/128216
§ 371 (c)(1),
(2) Date: Mar. 7, 2023

(87) PCT Pub. No.: WO2024/082333
PCT Pub. Date: Apr. 25, 2024

(65) Prior Publication Data

US 2024/0189802 A1 Jun. 13, 2024

(30) Foreign Application Priority Data

Oct. 21, 2022 (CN) ......................... 202211291150.3

(51) Int. Cl.
*B01J 27/24* (2006.01)
*C07D 317/26* (2006.01)

(52) U.S. Cl.
CPC ............ *B01J 27/24* (2013.01); *C07D 317/26* (2013.01)

(58) Field of Classification Search
CPC ........................................................ B01J 27/24
See application file for complete search history.

(56) References Cited

U.S. PATENT DOCUMENTS 4,332,729 A * 6/1982 Renga .................. C07D 317/46 549/229

* cited by examiner

*Primary Examiner* — Golam M Shameem
(74) *Attorney, Agent, or Firm* — Hodgson Russ LLP

(57) ABSTRACT

The present disclosure provides a use of a catalyst for catalyzing a reaction of an epoxide compound and carbon dioxide, the catalyst includes a spirocyclic compound including at least one compound of formula (1):

formula (1)

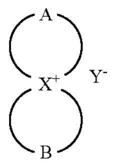

where X is selected from nitrogen, or phosphorus; Y is selected from halogens; A and B are independently selected from materials having formulae (a) to (d). Compared with catalysts with a non-spirocyclic structure or Lewis acid metal catalysts, the catalyst including the spirocyclic compound having the structural shown in formula 1 has the advantages of better catalytic effect, more stable performance and longer service life when catalyzing the reaction of the epoxy compounds and carbon dioxide. The present catalyst has both high efficiency and safety, and thus has broad application prospects.

15 Claims, 1 Drawing Sheet

SPIROCYCLIC COMPOUND CONTAINING CATALYST FOR USE IN CATALYZING REACTION OF EPOXIDE COMPOUND AND CARBON DIOXIDE

CROSS-REFERENCE TO RELATED APPLICATIONS

This application is a national phase of International Application No. PCT/CN2022/128216, filed Oct. 28, 2022, which claims priority to Chinese Patent Application No. 202211291150.3, filed Oct. 21, 2022, the entire disclosures of which are incorporated herein by reference.

FIELD

The present disclosure relates to the technical field of chemical synthesis, and specifically relates to use of a catalyst including a spirocyclic compound for catalyzing a reaction of an epoxide compound and carbon dioxide.

BACKGROUND

Carbon dioxide is a main greenhouse gas causing global warming, and it is also an inexhaustible, cheap, nontoxic and recyclable green carbon resource on the earth. Realizing the utilization of the carbon dioxide resource has a strategic significance for reducing carbon dioxide emissions, improving the environment, and reducing dependence on fossil fuels. The effective immobilization of carbon dioxide has become one of the most challenging topics in this century, and the synthesis of cyclic carbonate is one of the immobilization routes. In recent years, cyclic carbonate, as a high value-added chemical, has been widely used in fine chemical industry, lithium battery manufacturing, polycarbonate and polyurethane synthesis. However, the preparation of cyclic carbonate by cycloaddition of carbon dioxide and an epoxide compound is a green chemical method with nearly 100% atomic economy, which has been paid attention to by academia and industry.

At present, the reported production of cyclic carbonates mostly uses binary catalysts composed of Lewis acid metals and Lewis bases. The Lewis metals include alkali metal halides, alkaline earth metal halides, transition metal salts, transition metal complexes, or tetradentate Schiff alkali metal complexes. The Lewis bases include organic bases, ammonium salts, imidazole salts, solid bases (such as metal oxides), crown ethers, or molecular sieves, etc. These catalyst systems have problems, such as low catalytic activity, poor stability, harsh reaction conditions, use of highly toxic organic solvents, and high catalyst cost.

SUMMARY

The present disclosure provides in embodiments a method for preparing a cyclic carbonate by using a catalyst for catalyzing a reaction of an epoxide compound and carbon dioxide in which the catalyst includes a spirocyclic compound including at least one compound of formula (1):

formula (1)

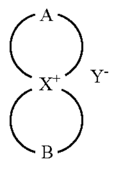

where X is selected from nitrogen, or phosphorus; Y is selected from halogens; A and B are independently selected from the following formulae with a sign * representing a bonding position:

formula (a)

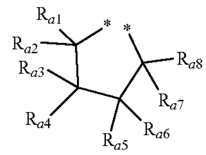

formula (b)

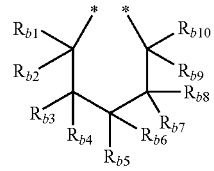

formula (c)

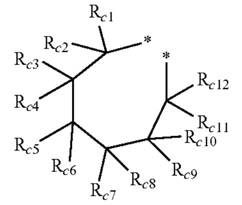

formula (d)

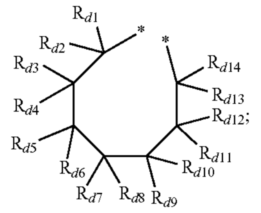

$R_{a1}$-$R_{a8}$, $R_{b1}$-$R_{b10}$, $R_{c1}$-$R_{c12}$, and $R_{d1}$-$R_{d14}$ are independently selected from H, or a C1-C5 alkyl group.

The method includes: dissolving the catalyst in a cyclic carbonate to obtain a mixed solution, and adding the epoxide compound to the mixed solution, and introducing carbon dioxide to adjust a pressure of a reaction system to allow the epoxide compound to react with carbon dioxide to generate the cyclic carbonate.

DETAILED DESCRIPTION

Figure 1:
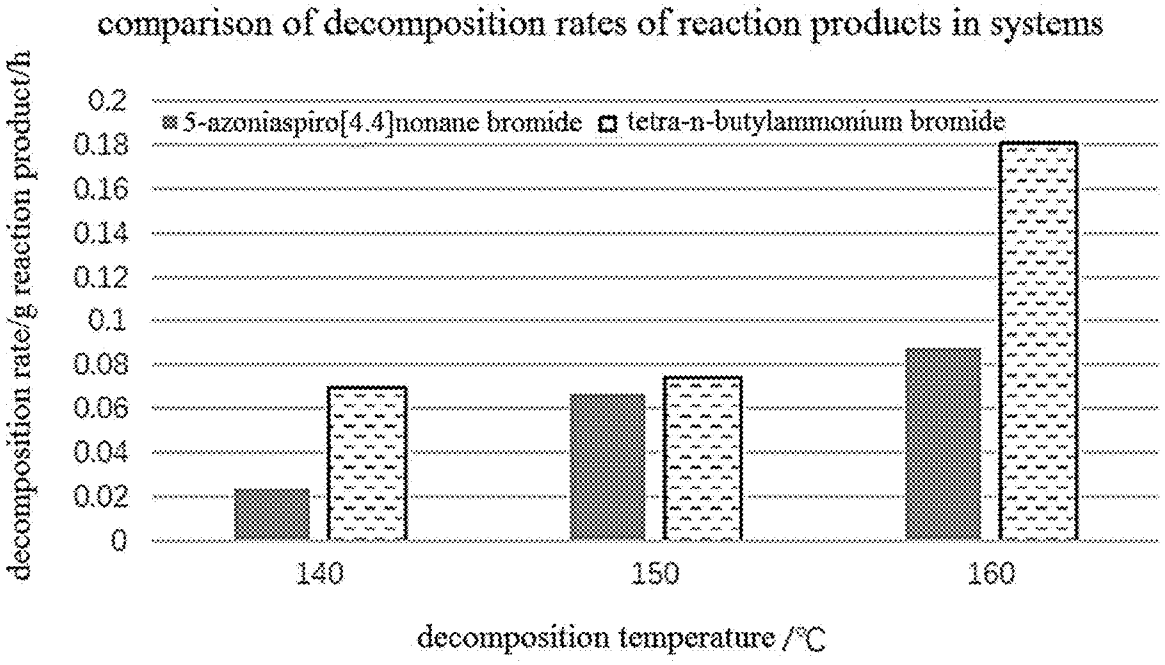
FIG. 1 shows detection results of a reverse reaction of a reaction of generating ethylene carbonate (EC) from an ethylene oxide and carbon dioxide catalyzed by 5-azoniaspiro[4.4]nonane bromide and tetra-n-butylammonium bromide.

Experimental methods in which specific conditions are not specified in the following embodiments of the present disclosure are usually in accordance with conventional conditions, or conditions recommended by manufacturers. Various common chemicals used in the embodiments are commercially available products.

Unless defined otherwise, all technical and scientific terms used herein have the same meaning as commonly understood by those skilled in the art to which the invention pertains. Terms used in the specification of the present disclosure are only for the purpose of describing specific embodiments, and are not intended to limit the present disclosure.

Terms "including", "having", and any variations thereof of the present disclosure are intended to cover non-exclusive inclusions. For example, a process, a method, an apparatus, a product, or an equipment that includes a series of steps is not limited to the listed steps or modules, but alternatively also includes steps that are not listed, or alternatively includes other steps inherent to these processes, methods, products or equipment.

Term "a plurality of" in the present disclosure refers to two or more. Term "and/or" describes an association relationship of associated objects, indicating that there may be three relationships. For example, A and/or B, may represent: A existing alone, A and B existing at the same time, and B existing alone. The character "/" generally indicates that the associated objects are items connected with "or".

One aspect of the present disclosure provides use of a catalyst for catalyzing a reaction of an epoxide compound and carbon dioxide, the catalyst includes a spirocyclic compound including at least one compound of formula (1):

formula (1)

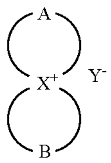

where X is selected from nitrogen, or phosphorus; Y is selected from halogens; A and B are independently selected from the following structures with a sign * representing a bonding position:

formula (a)

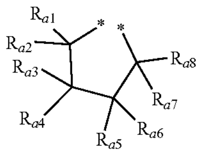

formula (b)

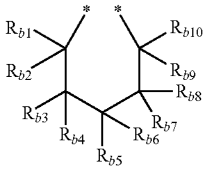

formula (c)

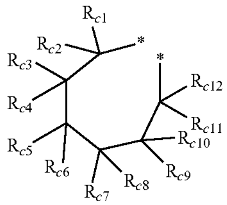

-continued formula (d)

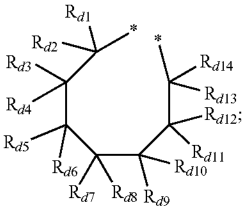

Ra1-Ra8, Rb1-Rb10, Rc1-Rc12, and Rd1-Rd14 are independently selected from H, or a C1-C5 alkyl group.

In some embodiments, at least one of A and B is selected from formula (a).

In some embodiments, Y is selected from Cl, Br, or I, preferably, Y is selected from Cl, or Br.

In some embodiments, the spirocyclic compound includes, but is not limited to:

1A

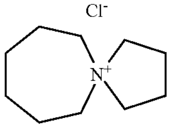

1B

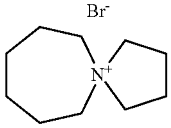

1C

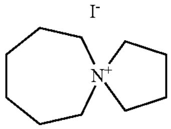

2A

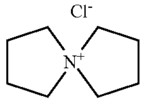

2B

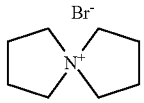

2C

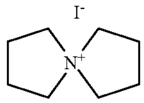

3A

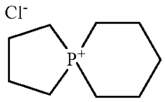

3B

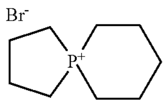

3C

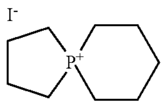

-continued

4A

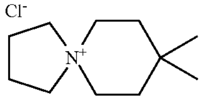

4B

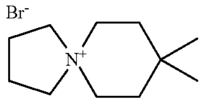

4C

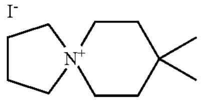

5A

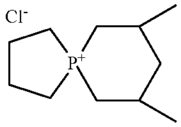

5B

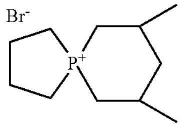

5C

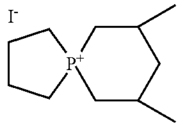

6A

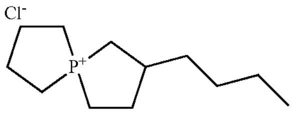

6B

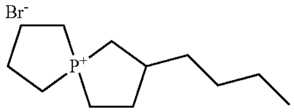

6C

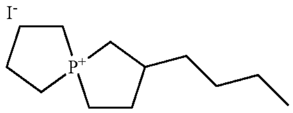

7A

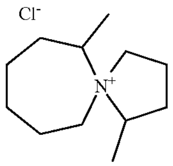

7B

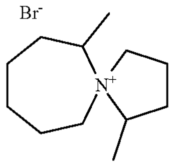

-continued

7C

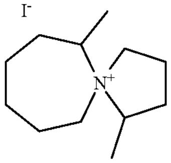

8A

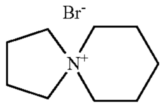

8B

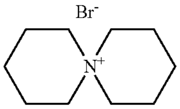

1A: 5-azoniaspiro[4.6]undecane chloride; 1B: 5-azoniaspiro[4.6]undecane bromide; 1C: 5-azoniaspiro[4.6]undecane iodide; 2A: 5-azoniaspiro[4.4]nonane chloride; 2B: 5-azoniaspiro[4.4]nonane bromide; 2C: 5-azoniaspiro[4.4] nonane iodide; 3A: 5-phosphaspiro[4.5] decane chloride; 3B: 5-phosphaspiro[4.5] decane bromide; 3C: 5-phosphaspiro[4.5]decane iodide; 4A: 8,8-dimethyl-5-azoniaspiro [4.5]decane chloride; 4B: 8,8-dimethyl-5-azoniaspiro[4.5] decane bromide; 4C: 8,8-dimethyl-5-azoniaspiro[4.5] decane iodide; 5A: 7,9-dimethyl-5-phosphaspiro[4.5]decane chloride; 5B: 7,9-dimethyl-5-phosphaspiro[4.5]decane bromide; 5C: 7,9-dimethyl-5-phosphaspiro[4.5]decane iodide; 6A: 2-butyl-5-phosphaspiro[4.4]nonane chloride; 6B: 2-butyl-5-phosphaspiro[4.4]nonane bromide; 6C: 2-butyl-5-phosphaspiro[4.4]nonane iodide; 7A: 1,6-dimethyl-5-azoniaspiro[4.6]undecane chloride; 7B: 1,6-dimethyl-5-azoniaspiro[4.6]undecane bromide; 7C: 1,6-dimethyl-5-azoniaspiro [4.6]undecane iodide; 8A: 5-azoniaspiro[4.5]decane bromide; 8B: 6-azoniaspiro[5.5]undecane bromide.

The preparation method of each of the above-mentioned compounds are known by those skilled in the art according to specific structure of the compound shown in formula (1) and the common knowledge in the field of chemical synthesis. For example, it may be prepared by the following method: carrying out a nucleophilic substitution reaction of materials M and N in presence of potassium carbonate in water to generate materials C (the compound shown in formula (1)) and D. The reaction formula is as follows:

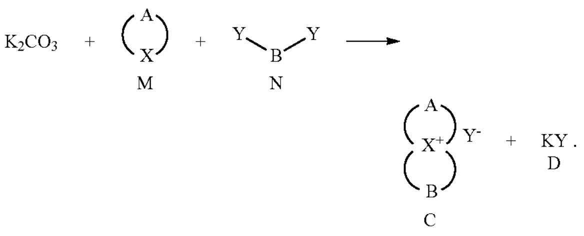

A solvent of the mixture including the materials C and D is evaporated. The remaining product is dissolved and filtered with a non-aqueous solvent, and is further decolorized, concentrated and crystallized, and dried to obtain a high-purity product C.

In some embodiments, the non-aqueous solvent includes one or more of ethanol, methanol, isopropanol, n-butanol, dimethyl carbonate, and acetonitrile. A dissolution temperature is in the range from a room temperature to 200° C., preferably in the range from 30° C. to 90° C.

In some embodiments, the method for separating the byproduct potassium salt D may be one of centrifuge flaking and filter filtration.

In some embodiments, the decolorization method may be one of activated carbon decolorization, hydrogen peroxide decolorization, and sodium hypochlorite decolorization.

In some embodiments, during the concentration and crystallization, a concentrating device may be one of a reaction kettle, an evaporator, a drum dryer, and a rake dryer.

In some embodiments, one of a rotary drum dryer, and a vacuum oven may be used for drying in the drying method.

Specifically, for example,

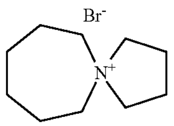 [SMILES: [Br-] ; C1CCC[N+]2(CC1)CCCC2]

(5-azoniaspiro[4.6]undecane bromide) may be prepared as follows.

Firstly, potassium carbonate was fully dissolved in water. 72 g of pyrrolidine, 244 g of 1,6-dibromohexane, and 244 g of ethanol were put into the potassium carbonate solution under magnetic stirring, and heated at 60° C. for 15 hours. Then, the temperature is increased for concentration and evaporation to dryness. The obtained solid was dissolved with isopropanol and after dissolving, 0.4 g of activated carbon was added and stirring was performed for 1 h for decoloration. After that, the activated carbon was filtered off, and the remaining solution was concentrated, recrystallized, filtered and dried. A white powder solid (purity 99.9%, yield 85%) was obtained.

After a lot of research, it is found that the catalyst including the spirocyclic compound shown in formula (1) has a better catalytic effect, a more stable catalytic performance, and a higher catalytic activity and selectivity even after a plurality of recycles when catalyzing the reaction of the epoxide compound and carbon dioxide to generate the cyclic carbonate compared with the traditional catalysts with non-spirocyclic structure or Lewis acid metal catalysts.

In some embodiments, the catalyst further includes at least one of water or alcohol. Further, water is present in the catalyst in a concentration of 2000 ppm or less. The alcohol is present in the catalyst in a concentration of 2000 ppm or less. The presence of the appropriate amount of water and/or alcohol does not affect the catalytic effect of the spirocyclic compound.

In some preferred embodiments, the alcohol is selected from at least one of methanol, ethanol, propanol, isopropanol or n-butanol.

In some embodiments, the epoxide compound is at least one selected from the compounds shown in formula (2):

formula (2)

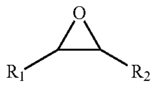

where when R1=H, R2 is one of H (ethylene oxide), CH3 (propylene oxide), CH2Cl (epichlorohydrin), C2H3 (epoxybutene), C4H9O (2-propoxymethyl ethylene oxide), C4H9 (epoxyhexane), C6H5 (styrene oxide), C8H7O (2-(phenoxymethyl) ethylene oxide), when R1≠H, the epoxide compound used is epoxycyclohexane.

The epoxide compound is preferably at least one of ethylene oxide or propylene oxide in terms of reaction efficiency, economic benefit and the like.

An initial concentration of the epoxide compound in the system is in a range of 1 to 15 wt %.

In some embodiments, the reaction includes steps of: dissolving the catalyst in a cyclic carbonate to obtain a mixed solution, adding an epoxide compound to the mixed solution, and introducing carbon dioxide to adjust a pressure of a reaction system to allow the epoxide compound to react with carbon dioxide to generate a cyclic carbonate.

In some embodiments, a mass percent concentration of the spirocyclic compound in the mixed solution is in a range from 0.5 to 10%; preferably from 1 to 5%.

Specifically, the mass percent concentration of the spirocyclic compound in the mixed solution may be 0.5%, 0.8%, 1%, 1.2%, 1.5%, 1.8%, 2%, 2.5%, 2.7%, 3%, 3.3%, 3.6%, 4%, 4.25%, 4.5%, 4.75%, 5%, 5.5%, 6%, 7.5%, 8%, 8.5%, 9.2%, 9.5%, or 10%.

In some embodiments, a temperature of the reaction is in a range from 100 to 200° C.; preferably, in a range from 120 to 170° C.

In some embodiments, a pressure of the reaction is in a range from 0.5 to 10 MPa; preferably, in a range from 1 to 5 MPa.

In some embodiments, a reaction time is in a range from 0.3 h to 20 h; preferably, in a range from 0.5 h to 15 h.

In some embodiments, a general formula of the catalyst for catalyzing the reaction of the epoxide compound and carbon dioxide is:

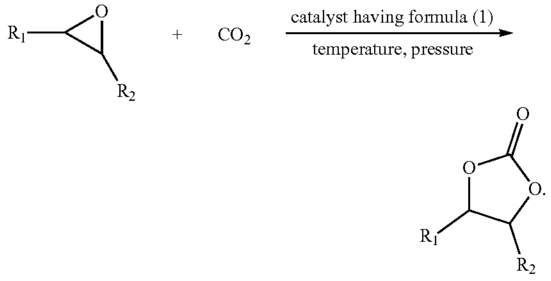

The present disclosure will be described with reference to specific examples below.

Example 1

This example provides a method for preparing a cyclic carbonate using 5-azoniaspiro[4.4]nonane bromide as a catalyst, and a reaction formula is as follows:

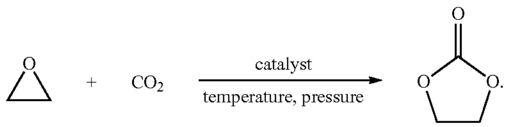

Implementation method: preparing the 5-azoniaspiro[4.4] nonane bromide and a target product ethylene carbonate into a solution with a catalyst concentration of 1 wt % in advance, adding 2 ml of ethylene oxide into a 25 mL stainless steel autoclave with a tetrafluoro liner, sealing the autoclave, charging carbon dioxide at an amount to reach an appropriate pressure, slowly increasing the temperature of the autoclave to 140° C., and controlling the carbon dioxide pressure to 3 MPa, reacting for 1 h, cooling to the room temperature, releasing the pressure, absorbing the carbon dioxide with a saturated sodium carbonate solution, analyzing the composition of the reaction solution by gas chromatography, and calculating an increase amount of the target product. In this example, the single-pass conversion of ethylene oxide is 95%, the product selectivity is >99%, and the yield is 94%.

Example 2

This example provides a method for preparing a cyclic carbonate using 5-azoniaspiro[4.6]undecane bromide as a catalyst, and a reaction formula is the same as that of EXAMPLE 1.

Implementation method: preparing the 5-azoniaspiro[4.6]undecane bromide and a target product ethylene carbonate into a solution with a catalyst concentration of 1.5 wt % in advance, adding 3 ml of ethylene oxide into a 25 mL stainless steel autoclave with a tetrafluoro liner, sealing the autoclave, charging carbon dioxide at an amount to reach an appropriate pressure, slowly increasing the temperature of the autoclave to 145° C., controlling the carbon dioxide pressure to 3 MPa, reacting for 1 h, cooling to the room temperature, releasing the pressure, absorbing the carbon dioxide with a saturated sodium carbonate solution, analyzing the composition of the reaction solution by gas chromatography, and calculating an increase amount of the target product. In this example, the single-pass conversion of ethylene oxide is 92%, the product selectivity is >99%, and the yield is 91%.

Example 3

This example provides a method for preparing a cyclic carbonate using 1,6-dimethyl-5-azoniaspiro[4.6]undecane iodide and 2000 ppm of water as a catalyst, and a reaction formula is as follows:

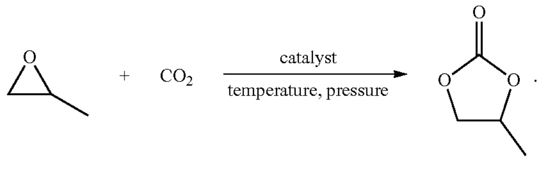

Implementation method: preparing the catalyst and a target product propylene carbonate into a solution with a 1,6-dimethyl-5-azoniaspiro[4.6]undecane iodide concentration of 2 wt % in advance, adding 2.4 ml of propylene oxide into a 25 mL stainless steel autoclave with a tetrafluoro liner, sealing the autoclave, charging carbon dioxide at an amount to reach an appropriate pressure, slowly increasing the temperature of the autoclave to 130° C., controlling the carbon dioxide pressure to 2.8 MPa, reacting for 1 h, cooling to the room temperature, releasing the pressure, absorbing the carbon dioxide with a saturated sodium carbonate solution, analyzing the composition of the reaction solution by gas chromatography, and calculating an increase amount of the target product. In this example, the single-pass conversion of propylene oxide is 85%, the product selectivity is >99%, and the yield is 84%.

Example 4

This example provides a method for preparing a cyclic carbonate using 5-phosphaspiro[4.5]decane bromide as a catalyst, and a reaction formula is the same as that of EXAMPLE 3.

Implementation method: preparing the 5-phosphaspiro[4.5]decane bromide and a target product propylene carbonate into a solution with a catalyst concentration of 1.8 wt % in advance, adding 2.6 ml of propylene oxide into a 25 mL stainless steel autoclave with a tetrafluoro liner, sealing the autoclave, charging carbon dioxide at an amount to reach an appropriate pressure, slowly increasing the temperature of the autoclave to 135° C., controlling the carbon dioxide pressure to 2.8 MPa, reacting for 1h, cooling to the room temperature, releasing the pressure, absorbing the carbon dioxide with a saturated sodium carbonate solution, analyzing the composition of the reaction solution by gas chromatography, and calculating an increase amount of the target product. In this example, the single-pass conversion of propylene oxide is 88%, the product selectivity is >99%, and the yield is 87%.

Example 5

This example provides a method for preparing a cyclic carbonate using 2-butyl-5-phosphaspiro[4.4]nonane bromide and 1000 ppm of water as a catalyst, and a reaction formula is the same as that of EXAMPLE 3.

Implementation method: preparing the catalyst and a target product propylene carbonate into a solution with a 2-butyl-5-phosphaspiro[4.4]nonane bromide concentration of 2.0 wt % in advance, adding 3.3 ml of propylene oxide into a 25 mL stainless steel autoclave with a tetrafluoro liner, sealing the autoclave, charging carbon dioxide at an amount to reach an appropriate pressure, slowly increasing the temperature of the autoclave to 150° C., controlling the carbon dioxide pressure to 3.5 MPa, reacting for 0.8 h, cooling to the room temperature, releasing the pressure, absorbing the carbon dioxide with a saturated sodium carbonate solution, analyzing the composition of the reaction solution by gas chromatography, and calculating an increase amount of the target product. In this example, the single-pass conversion of propylene oxide is 86%, the product selectivity is >99%, and the yield is 85%.

Example 6

This example provides a method for preparing a cyclic carbonate using 8,8-dimethyl-5-azoniaspiro[4.5]decane bromide as a catalyst, and a reaction formula is the same as that of EXAMPLE 1.

Implementation method: preparing the 8,8-dimethyl-5-azoniaspiro[4.5]decane bromide and a target product ethylene carbonate into a solution with a catalyst concentration of 1.8 wt % in advance, adding 3.2 ml of ethylene oxide into a 25 mL stainless steel autoclave with a tetrafluoro liner, sealing the autoclave, charging carbon dioxide at an amount to reach an appropriate pressure, slowly increasing the temperature of the autoclave to 160° C., controlling the carbon dioxide pressure to 3.0 MPa, reacting for 0.8 h, cooling to the room temperature, releasing the pressure, absorbing the carbon dioxide with a saturated sodium carbonate solution, analyzing the composition of the reaction solution by gas chromatography, and calculating an increase amount of the target product. In this example, the single-pass conversion of ethylene oxide is 87%, the product selectivity is >99%, and the yield is 86%.

Example 7

This example provides a method for preparing a cyclic carbonate using 5-azoniaspiro[4.5]decane bromide and 2000 ppm of ethanol as a catalyst, and a reaction formula is the same as that of EXAMPLE 1.

Implementation method: preparing the catalyst and a target product ethylene carbonate into a solution with a 5-azoniaspiro[4.5]decane bromide concentration of 10 wt % in advance, adding 3.3 ml of ethylene oxide into a 25 mL stainless steel autoclave with a tetrafluoro liner, sealing the autoclave, charging carbon dioxide at an amount to reach an appropriate pressure, slowly increasing the temperature of the autoclave to 105° C., controlling the carbon dioxide pressure to 5 MPa, reacting for 10 h, cooling to the room temperature, releasing the pressure, absorbing the carbon dioxide with a saturated sodium carbonate solution, analyzing the composition of the reaction solution by gas chromatography, and calculating an increase amount of the target product, the single-pass conversion of ethylene oxide was 87%, the product selectivity was >99%, and the yield was 83%.

Example 8

This example provides a method for preparing a cyclic carbonate using 6-azoniaspiro[5.5]undecane bromide, 500 ppm of water, and 1000 ppm of isopropanol as catalysts, and a reaction formula is the same as that of EXAMPLE 3.

Implementation method: preparing the catalyst and a target product propylene carbonate into a solution with a 6-azoniaspiro[5.5]undecane bromide concentration of 5 wt % in advance, adding 3.3 ml of propylene oxide into a 25 mL stainless steel autoclave with a tetrafluoro liner, sealing the autoclave, charging carbon dioxide at an amount to reach an appropriate pressure, slowly increasing the temperature of the autoclave to 120° C., controlling the carbon dioxide pressure to 1.5 MPa, reacting for 8 h, cooling to the room temperature, releasing the pressure, absorbing the carbon dioxide with a saturated sodium carbonate solution, analyzing the composition of the reaction solution by gas chromatography, and calculating an increase amount of the target product. In this example, the single-pass conversion of propylene oxide is 87%, the product selectivity is >99%, and the yield is 84%.

Example 9

This example provides a method for preparing a cyclic carbonate using 7,9-dimethyl-5-phosphaspiro[4.5]decane iodide as a catalyst, and a reaction formula is the same as that of EXAMPLE 3.

Implementation method: preparing the 7,9-dimethyl-5-phosphaspiro[4.5]decane iodide and a target product propylene carbonate into a solution with a catalyst concentration of 5 wt % in advance, adding 3.3 ml of propylene oxide into a 25 mL stainless steel autoclave with a tetrafluoro liner, sealing the autoclave, charging carbon dioxide at an amount to reach an appropriate pressure, slowly increasing the temperature of the autoclave to 170° C., controlling the carbon dioxide pressure to 2.5 MPa, reacting for 3 h, cooling to the room temperature, releasing the pressure, absorbing the carbon dioxide with a saturated sodium carbonate solution, analyzing the composition of the reaction solution by gas chromatography, and calculating an increase amount of the target product. In this example, the single-pass conversion of propylene oxide is 86%, the product selectivity is >99%, and the yield is 85%.

Example 10

This example provides a method for preparing a cyclic carbonate using 1,6-dimethyl-5-azoniaspiro[4.6]undecane chloride, 2000 ppm of water, and 2000 ppm of methanol as a catalyst, and a reaction formula is the same as that of EXAMPLE 3.

Implementation method: preparing the catalyst and a target product propylene carbonate into a solution with a 1,6-dimethyl-5-azoniaspiro[4.6]undecane chloride concentration of 6.5 wt % in advance, adding 3.3 ml of propylene oxide into a 25 mL stainless steel autoclave with a tetrafluoro liner, sealing the autoclave, charging carbon dioxide at an amount to reach an appropriate pressure, slowly increasing the temperature of the autoclave to 140° C., controlling the carbon dioxide pressure to 8 MPa, reacting for 15 h, cooling to the room temperature, releasing the pressure, absorbing the carbon dioxide with a saturated sodium carbonate solution, analyzing the composition of the reaction solution by gas chromatography, and calculating an increase amount of the target product. In this example, the single-pass conversion of propylene oxide is 85%, the product selectivity is >99%, and the yield is 85%.

Examples 11 TO 15

Specific experimental methods and steps of EXAMPLEs 11 to 15 are the same as those of EXAMPLE 2. Newly generated ethylene carbonate is separated and the ethylene oxide and carbon dioxide are introduced into the reaction system for further reaction(s). The catalyst used for one or more times and the number of the times is shown in Table 1.

TABLE 1

The number of times that the catalyst is used

| | Example | | | | |
|---|---|---|---|---|---|
| | 11 | 12 | 13 | 14 | 15 |
| Number of times | 1st | 2nd | 3rd | 4th | 5th |

Comparative Example 1

This comparative example provides a method for preparing a cyclic carbonate using tetra-n-butylphosphonium bromide as a catalyst.

Implementation method: preparing the tetra-n-butylphosphonium bromide and a target product ethylene carbonate into a solution with a catalyst concentration of 1.5 wt % in advance, adding 3 ml of ethylene oxide into a 25 mL stainless steel autoclave with a tetrafluoro liner, sealing the autoclave, charging carbon dioxide at an amount to reach an appropriate pressure, slowly increasing the temperature of the autoclave to 140° C., controlling the carbon dioxide pressure to 3 MPa, reacting for 1 h, cooling to the room temperature, releasing the pressure, absorbing the carbon dioxide with a saturated sodium carbonate solution, analyzing the composition of the reaction solution by gas chromatography, and calculating an increase amount of the target product. In this example, the single-pass conversion of ethylene oxide is 75%, the product selectivity is >97%, and the yield is 73%.

Comparative Example 2

This comparative example provides a method for preparing a cyclic carbonate using lithium bromide as a catalyst.

Implementation method: preparing the lithium bromide and a target product ethylene carbonate into a solution with a catalyst concentration of 1.5 wt % in advance, adding 3 ml of ethylene oxide into a 25 mL stainless steel autoclave with a tetrafluoro liner, sealing the autoclave, charging carbon dioxide at an amount to reach an appropriate pressure, slowly increasing the temperature of the autoclave to 145° C., controlling the carbon dioxide pressure to 3 MPa, reacting for 1 h, cooling to the room temperature, releasing the pressure, absorbing the carbon dioxide with a saturated sodium carbonate solution, analyzing the composition of the reaction solution by gas chromatography, and calculating an increase amount of the target product. In this example, the single-pass conversion of ethylene oxide is 52%, the product selectivity is >75%, and the yield is 39%.

Comparative Example 3

This comparative example provides a method for preparing a cyclic carbonate using zinc bromide and hexabutylguanidine bromide as a catalyst.

Implementation method: preparing the composite catalyst of zinc bromide and hexabutylguanidine bromide (a molar ratio of zinc bromide to hexabutylguanidine bromide is 1:6) and a target product propylene carbonate into a solution with a catalyst concentration of 2 wt % in advance, adding 2.4 ml of propylene oxide into a 25 mL stainless steel autoclave with a tetrafluoro liner, sealing the autoclave, charging carbon dioxide at an amount to reach an appropriate pressure, slowly increasing the temperature of the autoclave to 130° C., controlling the carbon dioxide pressure to 2.8 MPa, reacting for 1 h, cooling to the room temperature, releasing the pressure, absorbing the carbon dioxide with a saturated sodium carbonate solution, analyzing the composition of the reaction solution by gas chromatography, and calculating an increase amount of the target product. In this example, the single-pass conversion of propylene oxide is 78%, the product selectivity is >99%, and the yield is 77%.

Comparative Example 4

This comparative example provides a method for preparing a cyclic carbonate using tetrapropyl ammonium bromide as a catalyst.

Implementation method: preparing the tetrapropyl ammonium bromide and a target product ethylene carbonate into a solution with a catalyst concentration of 1.5 wt % in advance, adding 3 ml of ethylene oxide into a 25 mL stainless steel autoclave with a tetrafluoro liner, sealing the autoclave, charging carbon dioxide at an amount to reach an appropriate pressure, slowly increasing the temperature of the autoclave to 145° C., controlling the carbon dioxide pressure to 3 MPa, reacting for 1 h, cooling to the room temperature, releasing the pressure, absorbing the carbon dioxide with a saturated sodium carbonate solution, analyzing the composition of the reaction solution by gas chromatography, and calculating an increase amount of the target product. In this example, the single-pass conversion of propylene oxide is 72%, the product selectivity is >95%, and the yield is 68%.

Comparative Examples 5 to 9

Specific experimental methods and steps of COMPARATIVE EXAMPLEs 5 to 9 are the same as those of COMPARATIVE EXAMPLE 4. The newly generated ethylene carbonate is separated and the ethylene oxide and carbon dioxide are introduced into the system of COMPARATIVE EXAMPLE 4 for further reaction(s). The number of times that the catalyst is used is shown in Table 2.

TABLE 2

The number of times that the catalyst is used

| | Comparative Example | | | | |
|---|---|---|---|---|---|
| | 5 | 6 | 7 | 8 | 9 |
| Number of times | $1^{st}$ | $2^{nd}$ | $3^{rd}$ | $4^{th}$ | $5^{th}$ |

The catalytic activities of the catalysts in the preparation methods of the above examples and comparative examples are tested.

Test results of the catalyst activities in Examples 1 to 10 and Comparative Examples 1 to 4 are shown in Table 3.

TABLE 3

Test results of the catalyst activities

| IE/CE | Catalyst species | Epoxide | Temperature/ ° C. | Pressure/ Mpa | Time/ h | SPC of epoxide/% | Selectivity/ % | yield/ % |
|---|---|---|---|---|---|---|---|---|
| IE1 | 2-butyl-5-phosphaspiro [4.4]nonane bromide | ethylene oxide | 140 | 3 | 1 | 95 | >99 | 94 |
| IE2 | 5-azoniaspiro [4.6]undecane bromide | ethylene oxide | 145 | 3 | 1 | 92 | >99 | 91 |
| IE3 | 1,6-dimethyl-5-azoniaspiro [4.6]undecane iodide + 2000 ppm of water | propylene oxide | 130 | 2.8 | 1 | 85 | >99 | 84 |
| IE4 | 5-phosphaspiro[4.5]decane bromide | propylene oxide | 135 | 2.8 | 1 | 88 | >99 | 87 |
| IE5 | 2-butyl-5-phosphaspiro [4.4]nonane bromide + 1000 ppm of water | propylene oxide | 150 | 3.5 | 0.8 | 86 | >99 | 85 |
| IE6 | 8,8-dimethyl-5-azoniaspiro [4.5]decane bromide | ethylene oxide | 160 | 3.0 | 0.8 | 87 | >99 | 86 |

TABLE 3-continued

| Test results of the catalyst activities | | | | | | | | |
|---|---|---|---|---|---|---|---|---|
| IE/CE | Catalyst species | Epoxide | Temperature/° C. | Pressure/Mpa | Time/h | SPC of epoxide/% | Selectivity/% | yield/% |
| IE7 | 5-azoniaspiro[4.5]decane bromide + 2000 ppm of ethanol | ethylene oxide | 105 | 5 | 10 | 87 | >99 | 83 |
| IE8 | 6-azoniaspiro[5.5] undecane bromide + 500 ppm of water + 1000 ppm of isopropanol | propylene oxide | 120 | 1.5 | 8 | 87 | >99 | 84 |
| IE9 | 7,9-dimethyl-5-phosphaspiro[4.5]decane iodide | propylene oxide | 170 | 2.5 | 3 | 86 | >99 | 85 |
| IE10 | 1,6-dimethyl-5-azoniaspiro [4.6]undecane chloride + 2000 ppm of water + 2000 ppm of methanol | propylene oxide | 140 | 8 | 15 | 85 | >99 | 85 |
| CE1 | tetra-n-butylphosphonium bromide | ethylene oxide | 140 | 3 | 1 | 75 | 97 | 73 |
| CE2 | lithium bromide | ethylene oxide | 145 | 3 | 1 | 52 | 75 | 39 |
| CE3 | zinc bromide + hexabutylguanidine bromide | propylene oxide | 130 | 2.8 | 1 | 78 | 99 | 77 |
| CE4 | tetrapropyl ammonium bromide | ethylene oxide | 145 | 3 | 1 | 72 | 95 | 68 |

SPC: single-pass conversion

Test results of the catalyst activities of Examples 11 to 15 are shown in Table 4.

TABLE 4

| Test results of the catalyst activities | | | | | |
|---|---|---|---|---|---|
| | Example | | | | |
| | 11 | 12 | 13 | 14 | 15 |
| Number of times | 1st | 2nd | 3rd | 4th | 5th |
| EO conversion/% | 92 | 92 | 92 | 92 | 91 |
| Product yield/% | 91 | 91 | 91 | 91 | 90 |
| Selectivity/% | >99 | >99 | >99 | >99 | >99 |

Test results of the catalyst activities of Comparative Examples 5 to 9 are shown in Table 5.

TABLE 5

| Test results of the catalyst activities | | | | | |
|---|---|---|---|---|---|
| | Comparative Example | | | | |
| | 5 | 6 | 7 | 8 | 9 |
| Number of times | 1st | 2nd | 3rd | 4th | 5th |
| EO conversion/% | 75 | 72 | 70 | 69 | 68 |
| Product yield/% | 73.5 | 70.5 | 68 | 75 | 64.6 |
| Selectivity/% | >98 | >97 | >97 | >96 | >95 |

It can be seen from the comparison between the catalyst activity results of Examples 1 to 10 and the catalyst activity results of Comparative Examples 1 to 4 that the spirocyclic compound of the present disclosure has better single-pass conversion of epoxide, selectivity and yield, and better catalytic activity when catalyzing the reaction of the epoxide compound and carbon dioxide to generate the cyclic carbonate. The presence of water and/or alcohol (in the appropriate amount) does not affect the catalytic effect of the spirocyclic compound.

It can be seen from the comparison between the test results of Examples 11 to 15 and the test results of Comparative Examples 5 to 9 that the catalytic effect of the catalyst of the present disclosure is more stable than that of the existing non-spirocyclic structure catalysts, and can still maintain the high catalytic activity, selectivity and yield after a plurality of recycles, and no significant change in the catalytic activity is observed. However, the catalytic activity, the selectivity and the yield of the non-spirocyclic catalyst are decreased after a plurality of recycles. This proves that the spirocyclic structure of the present disclosure can make the catalytic effect of the catalyst more stable and the service life longer.

Comparative Example 10: Catalyst System Stability Comparison 1

Take a reverse reaction of a reaction of generating EC from ethylene oxide and carbon dioxide as an example (that is, testing decomposition of EC in a catalyst system).

Implementation method: dissolving 5-azoniaspiro[4.4] nonane bromide and tetra-n-butylammonium bromide into ethylene carbonate, respectively, heating at different temperatures for 5 to 10 h, collecting generated gas of each heated reaction liquid system, detecting a concentration of ethylene oxide in the collected gas by using gas chromatography, and calculating a decomposition rate of ethylene carbonate in the different catalyst reaction systems.

As shown in FIG. 1, in a case where 5-azoniaspiro[4.4] nonane bromide is used as the catalyst, the reaction system is stable at a high temperature, a reverse reaction rate is lower than that in a case where tetra-n-butylammonium bromide is used as the catalyst, and the reverse reaction rate rises gently with the increase of the reaction temperature, which indicates that the reaction system of 5-azoniaspiro [4.4]nonane bromide catalyst is more stable.

Comparative Example 11: Catalyst System Stability Comparison 2

Take a reverse reaction of a reaction of generating EC from ethylene oxide and carbon dioxide as an example (that is, testing decomposition of EC in a catalyst system).

Implementation method: dissolving 5-azoniaspiro[4.6]undecane bromide and lithium bromide into ethylene carbonate, respectively, heating at different temperatures for 5 to 10 h, collecting generated gas of each heated reaction liquid system, detecting a concentration of ethylene oxide in the collected gas by using gas chromatography, and calculating a decomposition rate of ethylene carbonate in the different catalyst reaction systems.

Figure 2:
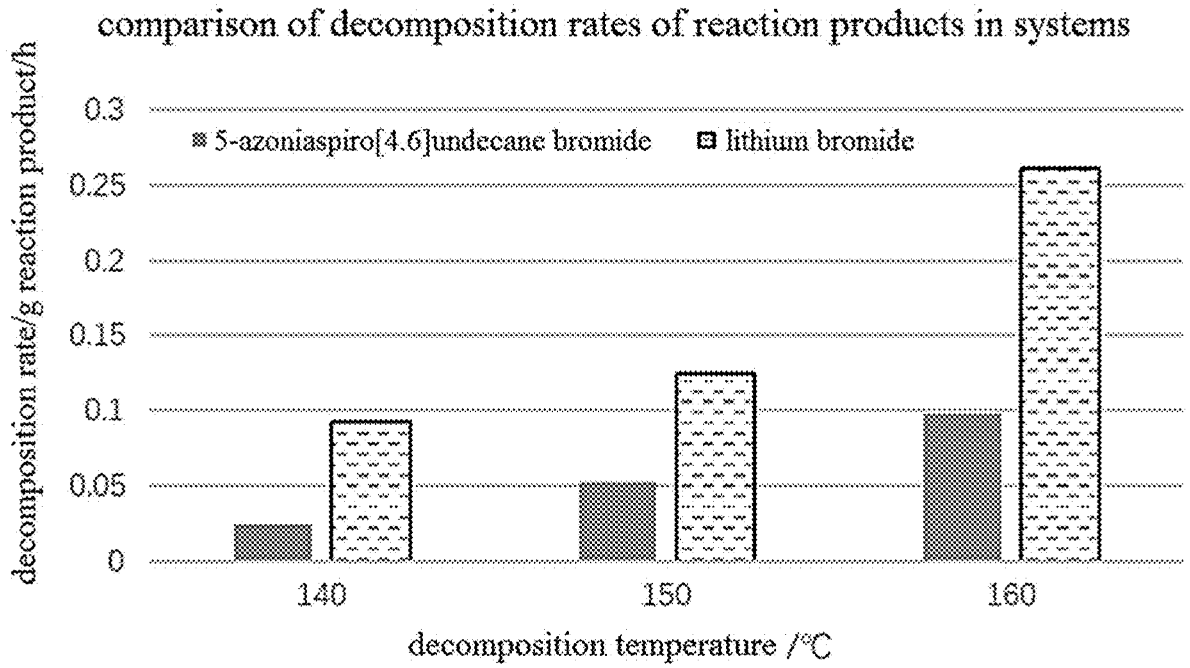
FIG. 2 shows detection results of a reverse reaction of a reaction of generating EC from an ethylene oxide and carbon dioxide catalyzed by 5-azoniaspiro[4.6]undecane bromide and lithium bromide.

As shown in FIG. 2, compared with the catalytic system of lithium bromide, the catalytic system of 5-azoniaspiro[4.6]undecane bromide is more stable at the high temperature, a reverse reaction rate is lower, and the reverse reaction rate rises gently with the increase of the reaction temperature, indicating that the catalytic system of 5-azoniaspiro[4.6]undecane bromide is more stable.

Based on the above, the catalyst provided by the present disclosure includes the compound with the spirocyclic structure, which has a more stable structure, and can still maintain the high catalytic activity, yield and selectivity after a plurality of use cycles compared with the existing non-spirocyclic structure catalysts or Lewis acid metal catalysts. Further, compared with the existing catalysts, the reaction system of the present disclosure is more stable at the high temperature, and the reverse reaction rate is lower, and the reverse reaction rate rises gently with the increase of the reaction temperature. It indicates that the spirocyclic compound of the present disclosure has the higher catalytic activity and the better stability when catalyzing the epoxide and carbon dioxide to synthesize the cyclic carbonate. Therefore, the synthesis process of the cyclic carbonate has high efficiency and safety, and has a broad application prospect.

The technical features of the above-mentioned embodiments can be combined. It should be noted that the above examples are not all the possible combinations of the technical features in the above-mentioned embodiments. As long as there is no contradiction between the technical features in the combinations, the combinations can be considered as being in the scope of the present disclosure.

The embodiments described above are merely representative of several embodiments of the present disclosure and are described in detail, but they are not to be construed as limiting the scope of the present disclosure. It is to be noted that those person skilled in the art could make several variations and modifications without departing from the concept of the present disclosure, which are within the scope of the present disclosure. Accordingly, the protection sought herein is as set forth in the appended claims.

What is claimed is:

1. A method for preparing a cyclic carbonate by using a catalyst for catalyzing a reaction of an epoxide compound and carbon dioxide, wherein the catalyst comprises a spirocyclic compound comprising at least one compound of formula (1):

formula (1)

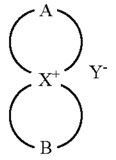

where X is selected from nitrogen, or phosphorus; Y is selected from halogens; A and B are both selected from the following formula (a) with a sign * representing a bonding position:

formula (a)

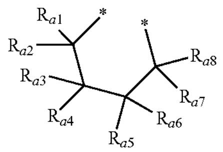

$R_{a1}$-$R_{a8}$ are independently selected from H, or a C1-C5 alkyl group;

wherein the method comprises:

dissolving the catalyst in a cyclic carbonate to obtain a mixed solution, and adding the epoxide compound to the mixed solution, and introducing carbon dioxide to adjust a pressure of a reaction system to allow the epoxide compound to react with carbon dioxide to generate the cyclic carbonate.

2. The method of claim 1, wherein Y is selected from Cl, Br, or I.

3. The method of claim 1, wherein the spirocyclic compound comprises 5-azoniaspiro[4.4]nonane halide.

4. The method of claim 1, wherein the spirocyclic compound comprises at least one selected from a group consisting of 5-azoniaspiro[4.4]nonane chloride; 5-azoniaspiro[4.4]nonane bromide; 5-azoniaspiro[4.4]nonane iodide; 2-butyl-5-phosphaspiro[4.4]nonane chloride; 2-butyl-5-phosphaspiro[4.4]nonane bromide; or 2-butyl-5-phosphaspiro[4.4]nonane iodide.

5. The method of claim 1, wherein the catalyst further comprises at least one of water or alcohol, water is present in the catalyst in a concentration of 2000 ppm or less, the alcohol is present in the catalyst in a concentration of 2000 ppm or less.

6. The method of claim 5, wherein the alcohol is selected from at least one of methanol, ethanol, propanol, isopropanol or n-butanol.

7. The method of claim 1, wherein the epoxide compound is selected from at least one of ethylene oxide or propylene oxide.

8. The method of claim 1, wherein a mass percent concentration of the spirocyclic compound in the mixed solution is in the range from 0.5 to 10%.

9. The method of claim 1, wherein a temperature of the reaction system is in a range from 100 to 200° C.

10. The method of claim 8, wherein the mass percent concentration of the spirocyclic compound in the mixed solution is in the range from 1 to 5%.

11. The method of claim 1, wherein the pressure of the reaction system is in a range from 0.5 to 10 MPa.

12. The method of claim 11, wherein the pressure of the reaction system is in a range from 1 to 5 MPa.

13. The method of claim 1, wherein a reaction time is in a range from 0.3h to 20h.

14. The method of claim 13, wherein the reaction time is in a range from 0.5h to 15h.

15. The method of claim 1, wherein an initial concentration of the epoxide compound in the mixed solution is in a range of 1 to 15 wt %.

* * * * *